US00RE36758E

United States Patent [19]

Fitz

[11] E Patent Number: Re. 36,758

[45] Reissued Date of Patent: Jun. 27, 2000

[54] ARTIFICIAL FACET JOINT

[76] Inventor: William R. Fitz, 6500 Mariemont Ave., Cincinnati, Ohio 45227

[21] Appl. No.: 09/016,776

[22] Filed: Jan. 30, 1998

Related U.S. Patent Documents

Reissue of:

[64] Patent No.: 5,571,191
Issued: Nov. 5, 1996
Appl. No.: 08/405,199
Filed: Mar. 16, 1995

[51] Int. Cl.[7] ..... A61F 2/44

[52] U.S. Cl. ..... 623/17; 606/61

[58] Field of Search ..... 623/16, 17, 18; 606/60–64, 69–71

[56] References Cited

U.S. PATENT DOCUMENTS

| | | | |
|---|---|---|---|
| 3,643,658 | 2/1972 | Steineman . | |
| 4,309,777 | 1/1982 | Patil . | |
| 4,502,161 | 3/1985 | Wall . | |
| 5,062,850 | 11/1991 | McMillan et al. | 623/17 |
| 5,071,437 | 12/1991 | Steffee | 623/17 |
| 5,456,722 | 10/1995 | McLeod et al. | 623/13 |

FOREIGN PATENT DOCUMENTS

| | | | |
|---|---|---|---|
| 0 322 334 | 6/1989 | European Pat. Off. | 606/61 |

*Primary Examiner*—Michael J. Milano
*Attorney, Agent, or Firm*—Gifford,Krass,Groh,Sprinkle, Patmore, Anderson & Citkowski

[57] ABSTRACT

A spinal facet prosthesis for a diseased or painful facet joint comprises a superior component and an inferior component. The superior component is roughly conical or pyramidal in form and is fastened to and over the distal tip of the inferior articular process of the diseased or painful facet joint. The inferior component is also roughly conical or pyramidal in form with one side elongated postero-medially and distally. The outer surface of the elongated side of the inferior component is of low friction, such as polished chromium coating or medical grade high-density polyethylene. The inferior component is fastened to and over the superior articular process of the diseased or painful facet joint. Each component is made of a biocompatible material. The inner surface of each component which is in contact with its respective articular process is coated with a porous coating to enhance the adhesion of each component to its respective articular process.

23 Claims, 3 Drawing Sheets

ARTIFICIAL FACET JOINT

Matter enclosed in heavy brackets [ ] appears in the original patent but forms no part of this reissue specification; matter printed in italics indicates the additions made by reissue.

BACKGROUND OF THE INVENTION

1. Field of the Invention

The present invention relates to an artificial spinal facet joint or prosthesis to replace a diseased, damaged, or otherwise painful facet joint.

2. Description of the Prior Art

This invention relates to an artificial facet joint comprised of two components, a superior articular component and an inferior articular component. The superior articular components is designed to replace the articular surface of the inferior articular process and the inferior articular component is designed to replace the articular surface of the superior articular process.

The function of the facet joint is to guide vertebral motion and to resist compression, rotation and shear. The facet joints share in supporting an estimated 10–15% of the load of the lumbar spine. The load upon the facets increases with extension of the spine. A large body of evidence exists to support the fact that the facet joint is a pain producing structure. This pain can be disabling to some degree in some people. This pain can be due to trauma to and/or degeneration of the facet joint.

An artificial facet joint should cover the articular surfaces of the painful facet joint. It should aid in guiding vertebral motion and be able to withstand compression, rotation and shear force. It should not cause compression to adjacent neural structures. The artificial facet joint should be both biocompatible and biostable so that the joint itself and its degradation by-products, if any exist, should not cause adverse tissue reactions.

It is a principal objective of this invention to provide an artificial facet joint that has these characteristics.

SUMMARY OF THE INVENTION

The present invention resides in a spinal facet joint prosthesis to replace a painful or otherwise damaged facet joint. The prosthesis is comprised of two components, a superior articular component (hereinafter, superior component) and an inferior articular component (hereinafter, inferior component). The superior component is designed to replace the damaged articular surface of the inferior articular process and the inferior component is designed to replace the damaged articular surface of the superior articular process.

The superior component is roughly one or pyramid in form with a rounded apex. This form is designed to conform to the tip of the inferior articular process so that the superior component can cover the entire distal portion of the inferior articular process.

The inferior component is also roughly cone or pyramid in form. This form is designed to conform to the tip of the superior articular process and to cover the distal portion of the inferior articular process. One side of the inferior component is concave and elongated postero-medially and distally to cover excursion of the superior component as it moves medially and inferiorly upon the inferior component. The anterior side of the inferior component is incomplete. It is shaped to contain a small pedicle to promote mechanical stability and to decrease neural damage when placed surgically in a patient.

Each component of the device of this invention is made of a biocompatible material such as stainless steel, unalloyed titanium, or a titanium-aluminum alloy. The elongated side of the inferior component has a low coefficient of friction so that it offers minimal resistance to the movement of the superior component. This may be accomplished by coating the outer surface of the elongated side with either polished chrome or a friction reducing material such as a medical-grade high density polyethylene.

Various methods are known for attaching each component of the device of this invention to its respective articular process. For example, attachment may be achieved with screws driven through the component and into the underlying bone. The attachment of any component to the underlying bone may be further enhanced by coating the interior surface of the component of the device with a multitude of small particles of the same material as the device and creating a porous inner surface to allow bony ingrowth into the porous inner surface thereby causing the device to become more firmly attached to the underlying bone.

A facet prosthesis embodying the present invention is intended to be constructed in various forms and shapes to replace any facet joint in the cervical, thoracic, or lumbar spine.

The object of this present invention to provide a novel prosthetic device for the facet joints of the spine.

It is the further object of the present invention to provide a prosthetic joint that will maintain the natural motion of the spine and not allow increased wear and tear to occur at adjacent levels.

Other objects, features, and advantages of the present invention will become apparent upon reading the following detailed description of the embodiments of the invention when taken in conjunction with the drawing and the appended claims.

BRIEF DESCRIPTION OF THE DRAWINGS

Further features of the present invention will become apparent from reading the following specification with reference to the accompanying drawings, in which.

DETAILED DESCRIPTION OF A PREFERRED EMBODIMENT

Figure 1:
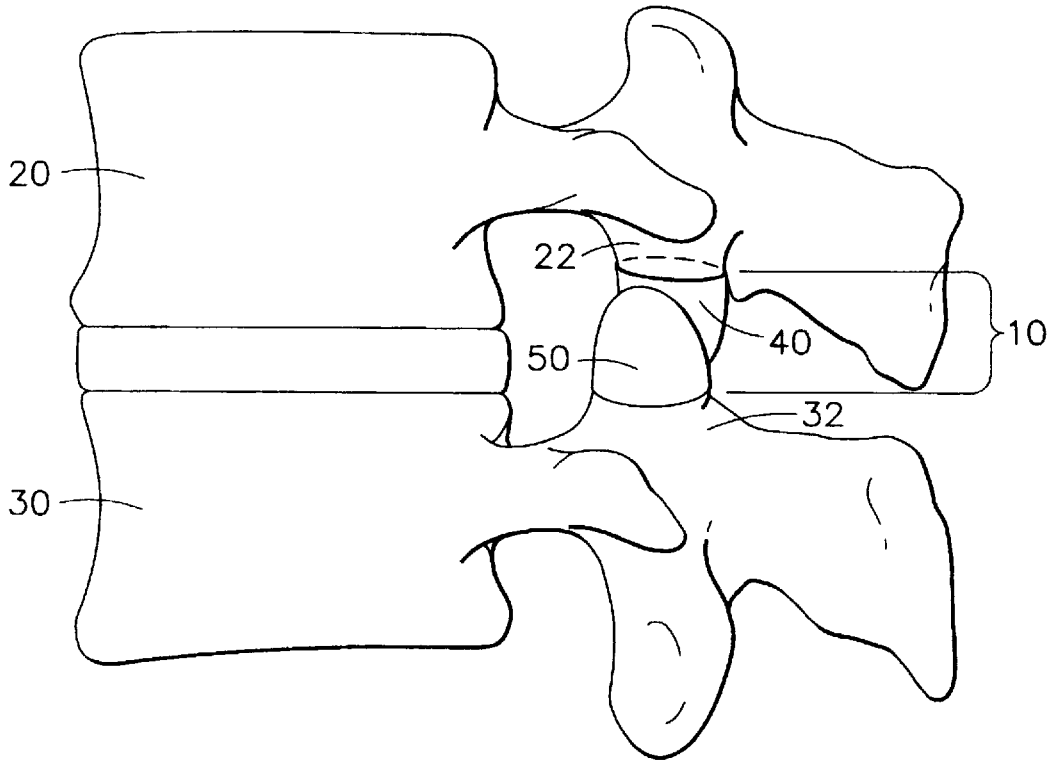
FIG. 1 is a side view of the spine with the prosthesis in place.
Figure 2:
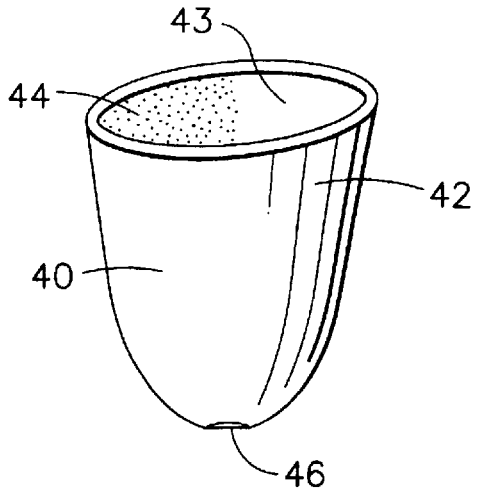
FIG. 2 is a perspective view of the superior articulating component.

In FIG. 1 the prosthesis 10 is shown in place between two adjacent lumbar vertebrae 20 and 30 of a human. The prosthesis 10 is composed of a superior articular component 40 and an inferior articular component 50.

The superior component 40 is roughly in the form of a hollow cone or a hollow pyramid with a rounded apex. It is designed to fit over the tip of the inferior articular process 22. The exact form of the superior component 40 is such that it generally conforms to the shape of the tip of the inferior articular process 22 so as to be a matching fit over it. The superior component 40 contains a hole 46 at its apex to allow the insertion of a screw 48 to firmly affix the superior component 40 to the inferior articular process 22.

Figure 3:
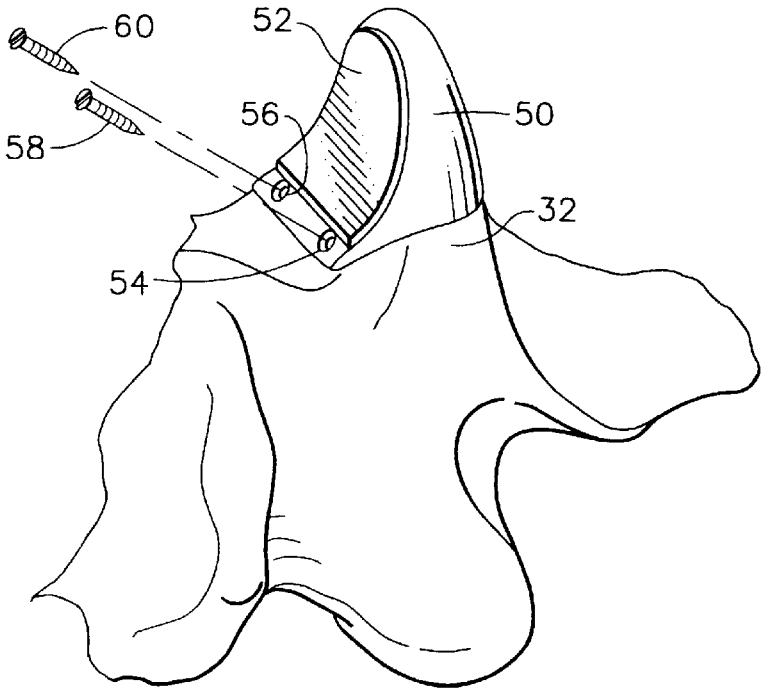
FIG. 3 is a perspective view of the inferior articular component covering the superior articular process.
Figure 4:
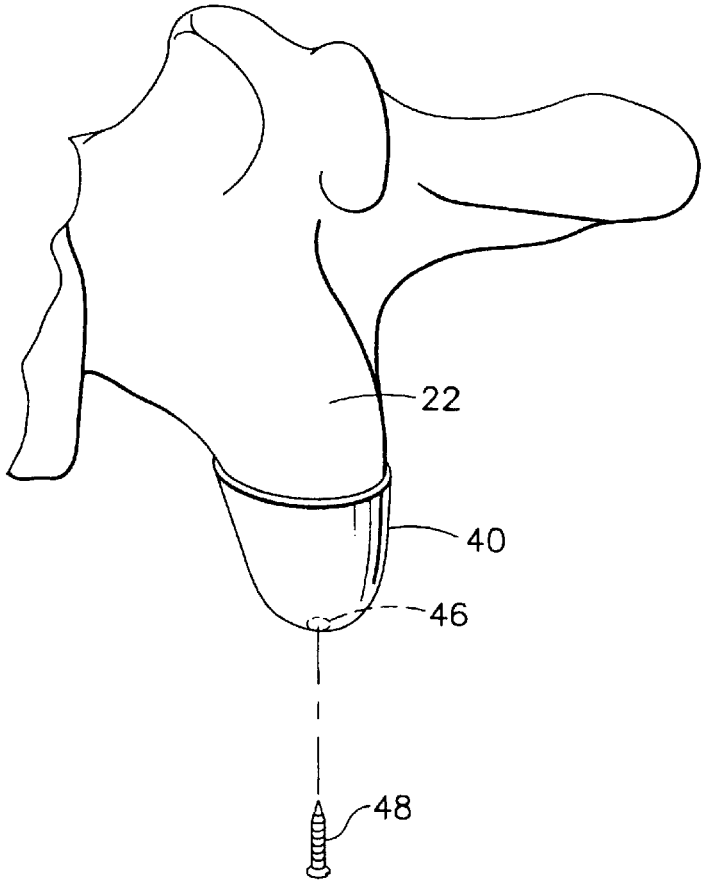
FIG. 4 is a perspective view of the superior articular component covering the inferior articular process.

In FIG. 3 the inferior articular component 50 is viewed posteriorly and is depicted in place over the tip of the superior articular process 32. The articular exterior surface 52 of this component is concave and elongated medially to cover the excursion of the superior component 40 as it moves inferiorly and medially over the elongated articular surface 52. The elongated articular surface 52 of this component has a low coefficient of friction so that there is a minimal resistance to the movement of the superior component 40 over it. There are a number of ways to make the articular surface 52 a low friction surface. For example, the surface may be made smooth and non-porous by applying a coating of polished chrome. Alternatively, a layer of a medical-grade high density polyethylene can be firmly attached to the elongated articular surface 52. Two holes 54 and 56 are placed in the distal portion of the elongated surface 52 to allow the insertion of two screws 58 and 60 which affix the inferior component 50 to the superior articular process 32.

Figure 5:
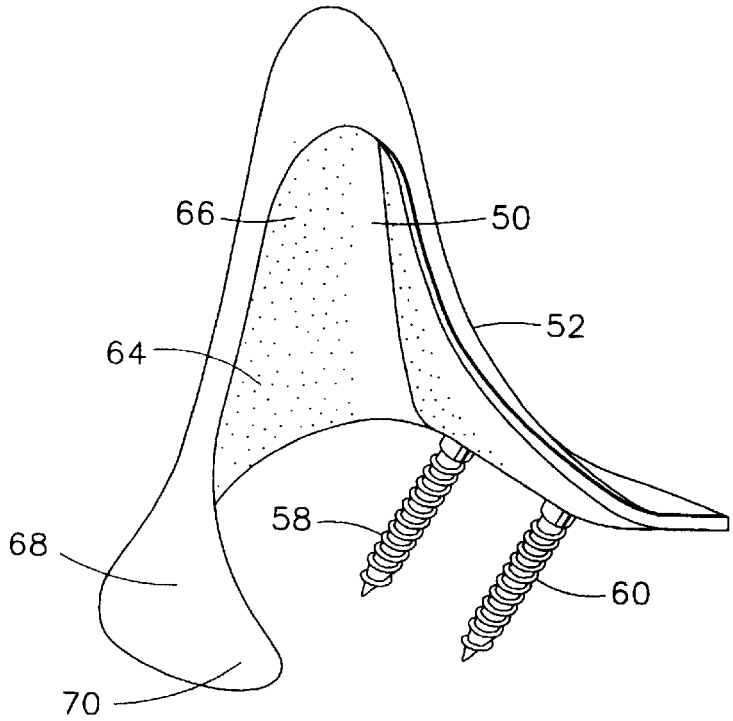
FIG. 5 is a perspective view of the inferior articular component.
Figure 6:
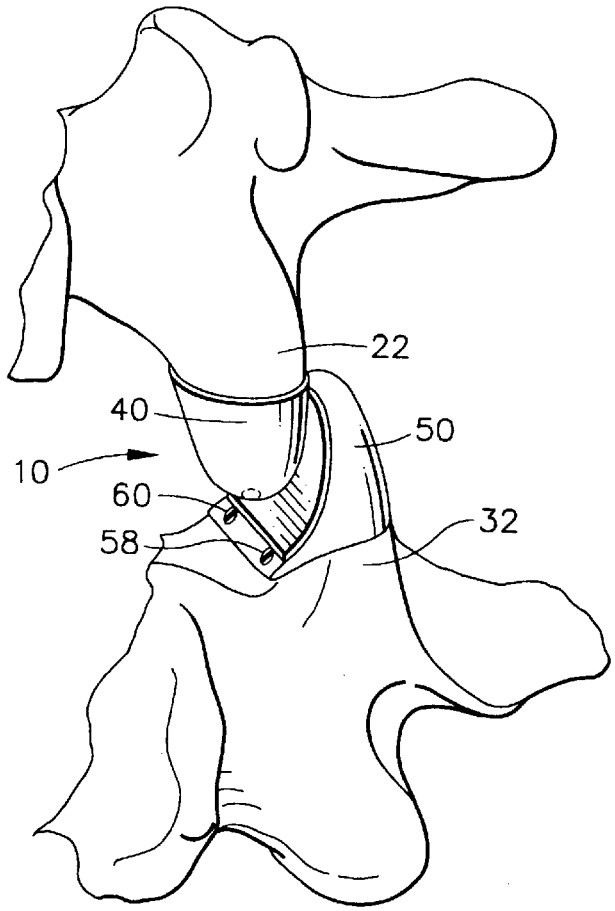
FIG. 6 is a perspective view of the superior articular component articulating with the inferior articular component.

As best shown in FIG. 5 the inferior component 50 is a hollow device with an incomplete anterior side 68. The incomplete anterior side is formed in the shape a small pedicle 70 for stability. The purpose of the incomplete anterior side 68 of the inferior component 50 is to facilitate the placement of the inferior component 50 over the superior articular process 32 and to reduce the risk of neural injury to the spinal nerve during the placement of the inferior component 50.

The adhesion of either the superior component 40 or the inferior component 50 or both to the underlying bone may be enhanced by applying a porous coating 44 and 66, respectively, to the inner surface of the superior component 43 or to the inner surface of the inferior component 64. In the preferred embodiment of this invention the porous material is of the same material as the component to which it is applied. There are many methods known to those skilled in the art for producing the porous coating. For example, the porous coating can be made up of small spherical particles that are attached to the interior surface by methods well known in the art. The porous coating will allow for bony ingrowth to occur and to firmly attach the component to the underlying bone.

Although this invention has been described in detail with particular reference to preferred embodiments, it will be understood that it is intended to cover all modifications, variations and equivalents within the spirit and scope of this invention as described before and as defined in the appended claims.

I claim:

1. A prosthetic device for implantation over a painful or otherwise damaged inferior articular process or [a] *an adjacent* superior articular process, or both, [of] *at the point where such processes interact within* a human spinal facet joint, *the device* comprising, a [superior] component [roughly in the form of a hollow cone or pyramid with a rounded apex] *having an outer surface adapted to* substantially [conforming] *conform* to the size and shape of the [distal tip of the inferior] *outer surface of said painful or otherwise damaged* articular process [so as to be a substantially matching fit over it;], *at least at the point where said painful or otherwise damaged articular process interacts with said adjacent articular process; and*

[an inferior component roughly in the form of a hollow cone or pyramid substantially conforming to the size and shape of the distal tip of the inferior articular process so as to be a substantially matching fit over it;

means for affixing said superior component to said distal tip of the inferior articular process;]

means for affixing said [inferior] component to said [distal tip of the superior] *painful or otherwise damaged* articular process.

2. The device of claim 1, wherein said [inferior] component has a concave and elongated exterior surface positioned in matching opposition to [the distal tip of the inferior] *the outer surface of said mating* articular process so as to provide a bearing surface [to said distal tip along its path] as it moves [medially and inferiorly over said elongated surface] *with respect thereto*.

3. The device of claim 2, wherein said elongated surface is smooth so as to reduce the resistance to [the] *said* movement [of said inferior articular process over said inferior component].

4. The device of claim 2, wherein said elongated surface is coated with non-porous polished chrome.

5. The device of claim 2, wherein a layer of medical-grade high density polyethylene is firmly affixed to said elongated surface.

6. The device of claim 1, wherein said means of affixing said [superior] component [to said distal tip of the inferior articular process is] *comprises* at least one screw passing through the apex of [the superior] *said* component and into the underlying [distal tip of the inferior articular process] *bone*.

7. The device of claim 1, wherein said means of affixing said [inferior] component [to said tip of the superior articular process is] *comprises* at least two screws passing through the distal portion of [the inferior] *said* component and into the underlying [distal tip of the superior articular process] *bone*.

8. The device of claim 1, wherein said [device] *component* is made of a biocompatible material.

9. The device of claim 1, wherein [the device] *said component* is made of stainless steel.

10. The device of claim 1, wherein [the device] *said component* is made of unalloyed titanium.

11. The device of claim 1, wherein [the device] *said component* is made of a titanium-aluminum alloy.

12. The device of claim 1, wherein [the] *said component includes an* inside [surfaces of said device are] *surface* coated with a porous coating.

13. The device of claim 12, wherein the material of said porous coating is the same as the material of said [device] *component*.

14. The device of claim [1] *20*, wherein said form of the inferior component has an incomplete side so as to form an open area in said inferior component so that said open area is superimposed over the spinal nerve at the superior articular process.

15. The device of claim 14, wherein said incomplete side is in the shape of a pedicle.

16. A prosthetic device for implantation over a painful or otherwise damaged inferior articular process [or a superior articular process, or both], of a human spinal facet joint, comprising, a superior component roughly in the form of a [hollow] cone or pyramid with a rounded apex [with a hole at the apex] *adapted to* substantially [conforming] *conform* to the size and shape of the distal tip of the inferior articular process [so as to be a substantially matching fit over it] *to be repaired with said component*[;]

[an inferior component roughly in the form of an incomplete hollow cone or pyramid substantially conforming to the size and shape of the distal tip of the inferior articular process so as to be a substantially matching fit over it with one side having a smooth concave and elongated surface positioned in matching opposition to the distal tip of the inferior articular process and to provide a bearing surface to said distal tip along its path as it moves medially and inferiorly over said elongated surface with at least two holes in the distal portion of said elongated surface and with an open area adjacent to said elongated surface formed by an incomplete side in the shape of a pedicle].

17. The device of claim 16, wherein [the] *said superior component includes an* inside [surfaces of the device are] *surface* coated with a porous coating.

*18. The device of claim 1, wherein said component is a superior component.*

*19. The device of claim 18, wherein said superior component is roughly in the form of a hollow cone or pyramid with a rounded apex adapted to substantially conform to the size and shape of the distal tip of the inferior articular process so as to be a substantially matching fit over it.*

*20. The device of claim 1, wherein said component is a inferior component.*

*21. The device of claim 20, wherein said inferior component roughly in the form of a hollow cone or pyramid adapted to substantially conform to the size and shape of the distal tip of the superior articular process so as to be a substantially matching fit over it.*

*22. A prosthetic device for implantation over a painful or otherwise damaged inferior articular process of a human spinal facet joint, comprising:*

*a superior component roughly in the form of a cone or pyramid with a rounded apex adapted to substantially conform to the size and shape of the distal tip of an inferior articular process to be repaired with said component.*

*23. In a human spinal facet joint wherein a portion of the outer surface of a superior articular process interacts with a portion of the outer surface of an inferior articular process, a method of relieving discomfort comprising the steps of:*

*installing a prosthetic device having an outer surface which replaces the outer surface of one or both of the superior and inferior articular processes, at least in the vicinity where said processes interact.*

* * * * *